US00PP37569P2

(12) United States Plant Patent
Gardner et al.

(10) Patent No.: US PP37,569 P2
(45) Date of Patent: Aug. 11, 2026

(54) PEACH TREE NAMED 'Sierra Snow II'

(50) Latin Name: *Prunus persica*
Varietal Denomination: Sierra Snow II

(71) Applicants: Lacey Marie Gardner, Modesto, CA (US); Tracee Louise Bettencourt, Modesto, CA (US)

(72) Inventors: Lacey Marie Gardner, Modesto, CA (US); Tracee Louise Bettencourt, Modesto, CA (US)

( * ) Notice: Subject to any disclaimer, the term of this patent is extended or adjusted under 35 U.S.C. 154(b) by 0 days.

(21) Appl. No.: 18/831,589

(22) Filed: May 22, 2025

(51) Int. Cl.
*A01H 5/08* (2018.01)
*A01H 6/74* (2018.01)

(52) U.S. Cl.
USPC ..... Plt./195

(58) Field of Classification Search
USPC ..... Plt./195, 196
See application file for complete search history.

(56) References Cited

U.S. PATENT DOCUMENTS

PP13,527 P2 * 1/2003 Zaiger ..... A01H 5/08
Plt./195

* cited by examiner

*Primary Examiner* — Susan Mccormick Ewoldt
*Assistant Examiner* — Zachariah Allan Kay

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, California, with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size, white flesh fruit.
3. Fruit with an attractive light red skin color.
4. Fruit having good flavor and eating quality with a good balance between acid and sugar.
5. Firm, freestone fruit with good storage and shipping quality.

1 Drawing Sheet

Botanical designation: *Prunus persica.*
Variety denomination: 'Sierra Snow II'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, California.

Prior varieties

Among the existing varieties of peach trees, which are known to us, and mentioned herein, 'Summer Sweet' Peach (U.S. Plant Pat. No. 8,070), and the proprietary non-patented peach seedling selection '20BD124'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, California as an open pollinated seedling selection from seed of our proprietary non-patented peach seedling selection with the field identification number '20BD124'. A large number of these open pollinated seedling selections were planted and grown on their own root system, during which time we recognized the desirable tree and fruit characteristics of the present seedling and selected it in 2017 for additional asexual propagation and commercialization.

ASEXUAL REPRODUCTION OF THE VARIETY

In 2017 asexual reproduction of the new and distinct variety of peach tree was by budding to 'Nemaguard' Rootstock (non-patented), as performed by us in our experimental orchard located near Modesto, California, and shows that reproductions run true to the original tree and all characteristics of the tree and its fruit are established and transmitted through succeeding asexual propagations.

SUMMARY OF THE NEW VARIETY

The present new and distinct variety of peach tree is of large size, upright growth and a regular and productive bearer of large size, white flesh, freestone fruit with good flavor and eating quality. The fruit is further characterized by its firm flesh and light red skin color. In comparison to its proprietary seed parent (20BD124) the fruit of the new variety has white flesh compared to yellow. In comparison to the commercial variety 'Summer Sweet' Peach (U.S. Plant Pat. No. 8,070) the fruit of the new variety is approximately 16 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, California, with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil, climatic conditions and cultural practices.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 5 consecutive years. No alternate bearing observed.

*Fertility*.—Self-fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 550 hours at or below 45° F.

Trunk:

*Size*.—Large, average circumference 27.9 cm at 25.4 cm above ground on a 7 year old tree.

*Stocky*.—Stocky.

*Texture*.—Medium shaggy, roughness increases with age.

*Color*.—Varies from 5YR 5/4 to 5YR 3/4.

Branches:

*Size*.—Medium. Average circumference 16.2 at 1.2 meters above ground. Crotch angle approximately 30°, increases with heavy crop load.

*Surface texture*.—New growth relatively smooth. Mature growth medium rough, roughness increases with age.

*Lenticels*.—Average number 29 in a 25.8 sq cm area. Average length 3.7 mm. Average width 1.5 mm. Color 5YR 5/8 to 7.5YR 4/8.

*Color*.—New growth varies from 2.5GY 5/6 to 5GY 6/8. Mature growth varies from 5YR 2/2 to 7.5YR 2/2, varies with age of growth.

Leaves:

*Size*.—Large. Average length 163.9 mm. Average width 46.8 mm.

*Form*.—Lanceolate.

*Apex*.—Acuminate.

*Base*.—Cuneate.

*Margin*.—Serrulate.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 11.0 mm. Average width 1.8 mm. Longitudinally grooved. Surface-glabrous. Color varies from 5GY 6/6 to 5GY 8/6.

*Glands*.—Type — reniform. Size — medium. Average length 1.5 mm. Average diameter 0.8 mm. Number varies from 1 to 2, average number 2. Located primarily on base of leaf blade and upper portion of petiole. Color varies from 7.5YR 3/4 to 5YR 3/4.

*Stipules*.—None present at time of measurement.

*Color*.—Upper surface varies from 5GY 3/6 to 7.5GY 3/4. Lower surface varies from 5GY 5/4 to 5GY 4/6. Midvein color 5GY 8/6 to 5GY 7/6.

Flower buds:

*Size*.—Large. Average length 20.9 mm. Average diameter 10.5 mm.

*Hardiness*.—Hardy with respect to California winters.

*Form*.—Conical, becoming elongated just before opening.

*Pedicel*.—Average length 3.6 mm. Average width 1.1 mm. Surface-glabrous. Color varies from 5GY 7/8 to 5R 2/6.

*Color*.—Varies from 5RP 8/4 to 5RP 7/10.

*Number of buds per spur*.—One.

Flowers:

*Blooming period*.—Date of First Bloom Mar. 1, 2024. Date of Petal Fall Mar. 11, 2024, varies slightly with climatic conditions.

*Size*.—Large. Average height 26.3 mm. Average diameter 27.5 mm.

*Petals*.—Number — normally five, alternately arranged to sepals. Size — large. Average length 16.5 mm. Average width 16.0 mm. Petal apex — rounded. Petal base-truncate. Form — obovate to orbicular. Arrangement — slightly overlapping. Margin — sinuate. Color varies from 5RP 8/4 to 5RP 7/10, fades with age of flower. Both upper and lower surfaces glabrous.

*Sepals*.—Number-normally five, alternately arranged to petals. Sepal apex — ovate. Size — medium to large. Average length 6.3 mm. Average width 5.2 mm. Shape — ovate to triangular. Margin — entire. Surface — upper surface glabrous, lower surface pubescent. Color- upper surface varies from 2.5GY 6/6 to 7.5R 2/4. Lower surface varies from 2.5GY 5/6 to 7.5R 2/6.

*Stamens*.—Average number per flower 31. On average, the stamens are even with the height of the petals.

Filament — average length 11.5 mm. Filament color varies from N 9.5/(white) to 2.5RP 2/8. Anther color varies from 7.5RP 9/2 to 7.5RP 8/4.

*Pollen*.—Self-fertile. Color varies from 2.5Y 8.5/10 to 5Y 7/10.

*Pistil*.—Normally one. Average length 14.0 mm. Position of stigma even with anthers. Surface — pubescent. Color varies from 2.5GY 8/4 to 2.5GY 7/6.

*Fragrance*.—Very slight.

*Color*.—Varies from 5RP 8/4 to 5RP 4/10.

*Pedicel*.—Average length 3.6 mm. Average width 1.1 mm. Color varies from 5GY 7/6 to 5R 2/6. Surface — glabrous.

*Number flowers per flower bud*.—One.

Fruit:

*Maturity when described*.—Firm ripe and read for consumption.

*Date of first picking*.—Jul. 21, 2024.

*Date of last picking*.—Jul. 31, 2024, varies slightly with climatic conditions.

*Size*.—Large. Average diameter axially 76.1 mm. Average transversely in suture plane 82.7 mm. Average weight 272.6 grams.

*Productivity*.—Trees often set several times the number of fruits needed for a full crop load.

*Form*.—Globose.

*Suture*.—Some fruit with slight suture, extends from base to apex.

*Ventral surface*.—Nearly smooth.

*Apex*.—Slightly retuse.

*Base*.—Retuse.

*Stem cavity*.—Rounded to slightly elongated in suture plane. Average depth 11.4 mm. Average diameter 12.1 mm.

Stem:

*Size*.—Small. Average length 8.3 mm. Average diameter 2.3 mm.

*Color*.—Varies from 2.5GY 5/6 to 2.5GY 4/6.

Flesh:

*Ripens*.—Evenly.

*Texture*.—Firm, meaty.

*Fibers*.—Few, small, tender.

*Firmness*.—Firm, comparable to other commercial varieties.

*Aroma*.—Slight.

*Amydgalin*.—Undetected.

*Eating quality*.—Good.

*Flavor*.—Good, with a good balance between acid and sugar.

*Juice*.—Moderate amount, enhances flavor.

*Acidity*.—Not available.

*Brix*.—Average Brix 13.6°, varies slightly with amount of fruit per tree and climatic conditions.

*Color*.—Varies from N 9.5/(white) to 7.5Y 9/4.

*Pit cavity*.—Average length 37.0 mm. Average width 25.0 mm. Average depth 10.2 mm. Color varies from 5R 3/8 to 7.5R 3/10.

Skin:

*Surface*.—Smooth.

*Pubescence*.—Moderate amount, short in length.

*Tendency to crack*.—None.

*Color*.—Ground color varies from N 9.5/(white) to 7.5Y 8.5/4. Overspread with 7.5R 4/10 to 7.5R 3/8.

*Tenacity*.—Tenacious to the flesh.

*Astringency*.—Slight to none.

Stone:

*Type*.—Freestone, weak adherence to flesh.

*Size*.—Large. Average length 35.4 mm. Average width 23.6 mm. Average thickness 18.4 mm.

*Form*.—Obovoid.

*Base*.—Flat.

*Apex*.—Pointed. Average length 3.7 mm.

*Surface*.—Slightly pitted throughout, pits vary from round to elongated.

*Sides*.—Unequal, one side extending further from the suture plane.

*Ridges*.—Extend from base to apex.

*Tendency to split*.—None.

*Color*.—Varies from 10R 2/4 to 2.5YR 2/4 when dry.

Kernel:

*Size*.—Large. Average length 18.0 mm. Average width 11.4 mm. Average depth 6.6 mm.

*Form*.—Ovate.

*Viability*.—Viable, complete embryo development.

*Skin color*.—Varies from 5Y 9/6 to 5Y 8.5/6.

Use:

*Dessert*.—Market — local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, California, no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, California.

The invention claimed is:

1. A new and distinct variety of peach tree (*Prunus persica*) named 'Sierra Snow II', substantially as herein illustrated and described.

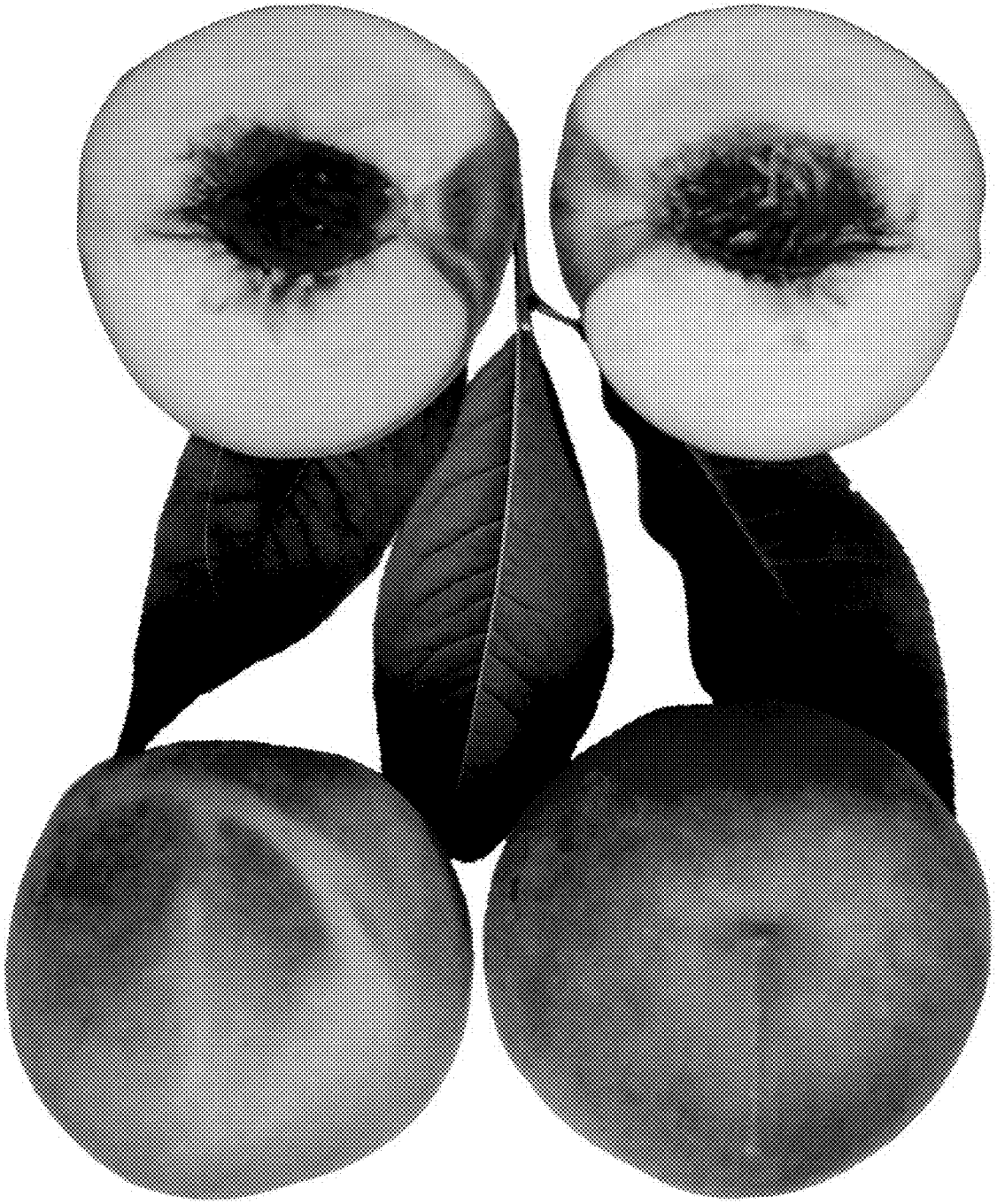

* * * * *